(12) United States Patent
Morley et al.

(10) Patent No.: US 7,956,323 B2
(45) Date of Patent: Jun. 7, 2011

(54) ION MOBILITY SPECTROMETER AND METHOD FOR DETERMINING AN ANALYTE SUBSTANCE OR AN ANALYTE SUBSTANCE MIXTURE IN THE PRESENCE OF A DOPANT MIXTURE BY MEANS OF AN ION MOBILITY SPECTROMETER

(75) Inventors: Stefan Morley, Lübeck (DE); Holger Bensch, Berlin (DE); Matthias Hurlebaus, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 519 days.

(21) Appl. No.: 12/165,803

(22) Filed: Jul. 1, 2008

(65) Prior Publication Data
US 2009/0032699 A1 Feb. 5, 2009

(30) Foreign Application Priority Data
Jul. 19, 2007 (DE) .................. 10 2007 033 547

(51) Int. Cl.
*B01D 59/44* (2006.01)

(52) U.S. Cl. ........ 250/288; 250/281; 250/282; 250/283; 250/287; 250/290

(58) Field of Classification Search .................. 250/281, 250/282, 283, 287, 288, 290
See application file for complete search history.

(56) References Cited

U.S. PATENT DOCUMENTS

| 4,551,624 | A  | * | 11/1985 | Spangler et al. ............... 250/287 |
| 5,234,838 | A  | * | 8/1993  | Bacon, Jr. ..................... 436/173 |
| 7,112,785 | B2 | * | 9/2006  | Laramee et al. ............... 250/288 |
| 7,253,413 | B2 | * | 8/2007  | Sauer et al. ............. 250/339.13 |
| 7,820,962 | B2 | * | 10/2010 | Wynn et al. .................... 250/282 |
| 2005/0085740 | A1 | * | 4/2005 | Davis et al. .................... 600/532 |

FOREIGN PATENT DOCUMENTS

| EP | 0 135 747 | 4/1985 |
| WO | WO 2006/123107 A1 | 11/2006 |

* cited by examiner

*Primary Examiner* — Bernard E Souw
*Assistant Examiner* — Michael J Logie
(74) *Attorney, Agent, or Firm* — McGlew and Tuttle, P.C.

(57) ABSTRACT

The present invention pertains to a method for determining an analyte substance or analyte substance mixture of ammonia and/or N-methyl-2-pyrrolidone as a component of a gas in the presence of a dopant mixture by means of an ion mobility spectrometer and to a corresponding ion mobility spectrometer.

20 Claims, 1 Drawing Sheet

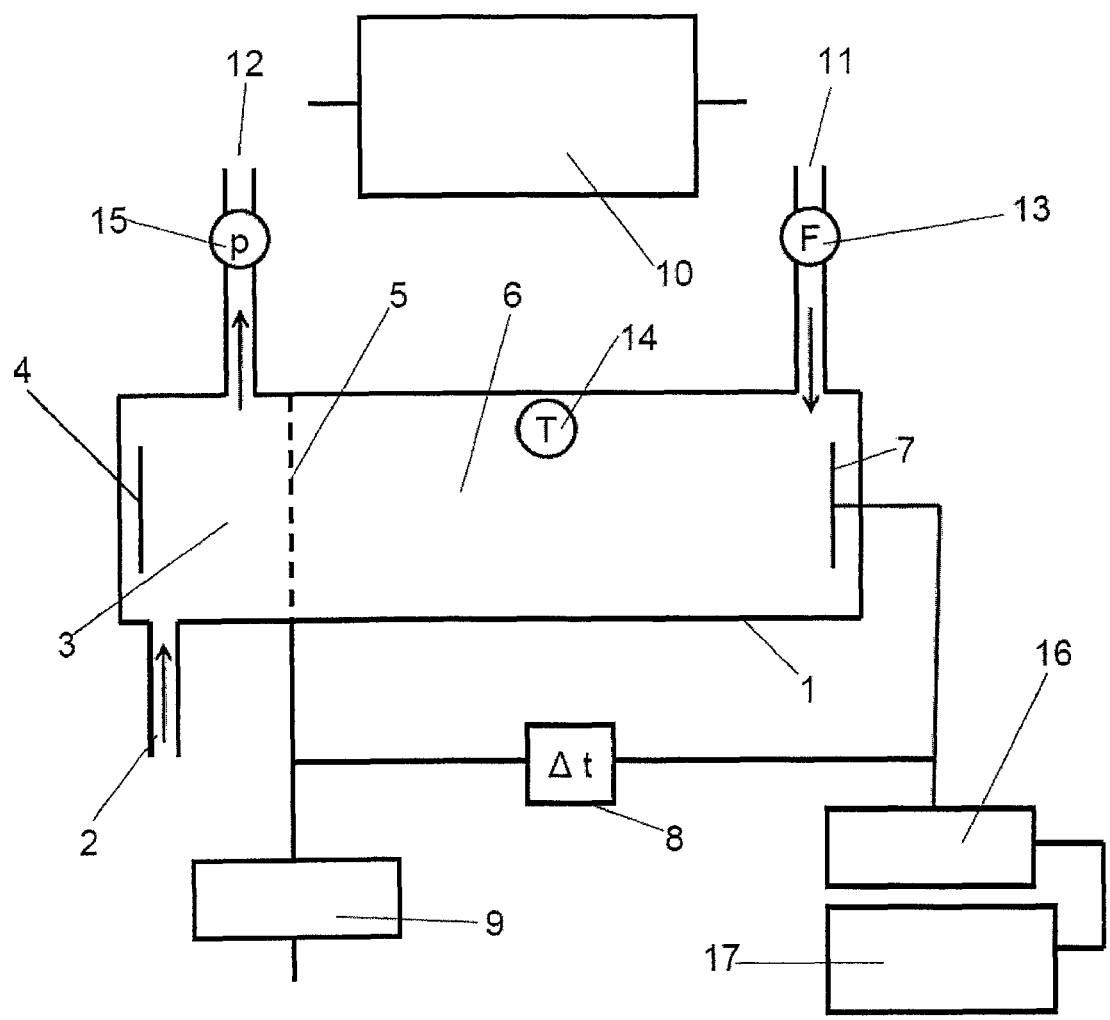

ION MOBILITY SPECTROMETER AND METHOD FOR DETERMINING AN ANALYTE SUBSTANCE OR AN ANALYTE SUBSTANCE MIXTURE IN THE PRESENCE OF A DOPANT MIXTURE BY MEANS OF AN ION MOBILITY SPECTROMETER

CROSS REFERENCE TO RELATED APPLICATIONS

This application claims the benefit of priority under 35 U.S.C. §119 of German patent application DE 10 2007 033 547.6 filed Jul. 19, 2007, the entire contents of which are incorporated herein by reference.

FIELD OF THE INVENTION

The present invention pertains to a method for determining an analyte substance or an analyte substance mixture as a component of a gas in the presence of a dopant mixture by means of an ion mobility spectrometer and to an ion mobility spectrometer.

BACKGROUND OF THE INVENTION

Ion mobility spectrometers (or IMS for short) are used for the highly sensitive detection of substances at low concentrations in the air or other gases. Gaseous substances are analyzed and continuously monitored in a plurality of applications, e.g., in environmental analytical procedures, in the control of chemical processes as well as in civil and military areas for detecting chemical warfare agents and explosives.

An ion mobility spectrometer comprises an analyzer cell, a means for ionizing samples of an analyte introduced into the cell, and a means for determining the times that the ions of the different substances present in the cells need to travel over a specific path length of the cell under the effect of an electrical field and with or against the force of a drift gas flow, which flows through the cell in a direction extending in the same direction as the electrical field or opposite the electrical field.

Low detection limits (lower ppb ranges and at times better), rapid response characteristic as well as moderate requirements in terms of hardware are among the advantages of this method. No additional sample preparation is necessary. Thus, the method is suitable for continuous monitoring, as it is necessary, e.g., for monitoring the air in the semiconductor industry.

Due to the low resolution compared to other spectral methods and a matrix-dependent sensitivity, the use of IMS as a measuring technique is limited and can be recommended only for substances with high proton or electron affinity.

The sensitivity is correlated with the presence of functional groups. The substances with high sensitivities include, e.g., amines or pyridines. Since the sensitivity of the signal pick-up is matrix-dependent, the residence time of the sample in the measuring system plays an important role for the quality of measurement. The transport of gases becomes increasingly more difficult with decreasing concentrations, because effects such as absorption and adsorption move increasingly into the foreground.

Since the composition of air shall be measured at the largest possible number of different measuring sites quasi on-line, sampling systems are used. The switchover between different intake lines increases the requirements to be imposed in terms of short residence time of the substances in the measuring system.

To suppress the matrix-dependent sensitivity, it is possible according to the state of the art to couple the IMS with other separation techniques. These separation techniques include GC (gas chromatography), HPLC (high performance liquid chromatography) in connection with electrospray for analyzing liquid samples, and MS (mass spectrometer) in various embodiments, e.g., TOF (time of flight). However, these solutions require a great effort in terms of hardware, cannot be automated, and lead to a prolongation of the analysis times.

A highly practicable method, which is, albeit, linked with special requirements, is the use of dopants (doping agents). Dopants can be introduced into the system permanently in the form of permeation tubes or dispensed with the analyte gas or drift gas in a sample-dependent manner. The rate of permeation depends on the design and the temperature. The concentration is obtained from the rate of permeation and the gas flow of the analysis gas flow. Substances with lower affinity (sensitivity) are suppressed by the dopant.

The introduction of an acetone dopant is described in EP 0 135 747 A2 (Spangler et al., 1985). Below a described concentration of the measured gas and drift gas moisture content, the drift time of the acetone dimer is independent from the moisture. The drift time of acetone can therefore be used for drift time calibration. The appearance of mixed clusters is described as well. EP 0 135 747 A2 pertains to the measurement of dimethyl phosphonate with an acetone dopant.

The use of DMMP (dimethyl methyl phosphonate) for the selective measurement of ammonia is described in U.S. Pat. No. 5,234,838 (Bacon, 1993). It is shown that the dimer ions of DMMP form clusters with ammonia. DMMP can be used as a starting compound for producing the nerve gas sarin and is hazardous for health.

The monitoring of the ammonia (CAS 7664-41-7) and N-methyl-2-pyrrolidone (NMP, CAS 872-50-4) concentrations is of particular interest for certain production processes but for other purposes as well. Both basic substances are used as process substances, and low concentrations of ammonia may also be of natural origin (e.g., exhalations from the human body). The natural concentration of ammonia in the air is approx. 5 to 10 ppb. Concentration ranges to be measured are normally between 0.1 ppb and 50 ppb. Furthermore, it is desirable for the measurement to be insensitive for this purpose to substances that are typically released in processes besides ammonia and N-methyl-2-pyrrolidone, e.g., solvents such as isopropyl alcohol. At the same time, ammonia and N-methyl-2-pyrrolidone shall be able to be determined each separately and together without a special hardware effort in terms of instruments.

SUMMARY OF THE INVENTION

It is an object of the present invention to make available a dopant or dopant mixture, which permits the simultaneous quantitative determination of ammonia and N-methyl-2-pyrrolidone and at least extensively reduces the action of interfering substances, for the highly specific determination of ammonia and N-methyl-2-pyrrolidone by means of IMS. The object is accomplished by a method of determining an analyte substance or an analyte substance mixture as a component of a gas in the presence of a dopant mixture with an ion mobility spectrometer. The analyte substance or the analyte substance mixture may be ammonia and/or N-methyl-2-pyrrolidone. The dopant mixture may comprise at least one phosphate ester and at least one ketone.

The phosphate ester/phosphate esters may be used at an analysis gas concentration of 5 to 50 and especially 10 to 20 $pg/m^3$.

The phosphate ester/phosphate esters may be a tri-(C1 to C12 carbon) phosphate ester, especially a triethyl phosphate.

The ketone/ketones may be used at an analyte substance concentration of 100 to 1,000 and especially 200 to 400 pg/m$^3$.

The ketone may be acetone.

Separate detection of ammonia and NMP, each as a component of a gas comprising a plurality of substances, is possible, but ammonia and NMP can also be detected simultaneously if these occur together.

It was surprisingly found that phosphate esters, especially triethyl phosphate (TEP), are suitable for this. A cluster of ammonia and TEP dimer is detected for the quantitative determination of ammonia. Without the presence of TEP, the detection of ammonia is highly sensitive to moisture and is interfered with even by trace amounts of water.

The reduced drift time of the TEP dimer advantageously does not depend on the temperature. NMP and TEP form a mixed cluster, which can be used for the quantification. The introduction of the TEP dopant is useful but not absolutely necessary for the detection of NMP alone.

Other investigations showed that the response and decay times of IMS can be substantially improved if ketones, especially acetone, are used as the dopant. This can be demonstrated quantitatively and qualitatively for NMP and ammonia. Acetone leads to a reduction of the absorption and adsorption effects and to the complete removal of the residual moisture on the gas-carrying assembly units of the detector. The acetone peaks are not used for the drift time calibration here.

The introduction of the sample through the internal heated sample loop system leads to a certain separation over time of the gas sample. Thus, if ammonia and NMP are present simultaneously, ammonia will enter the reaction space first, and NMP will enter it subsequently. It is thus not necessary for the separation of the substance to be complete.

Both ammonia and NMP are detected by means of mixed clusters with TEP. Since the proton affinities of these substances are substantially higher than those of isopropyl alcohol or comparable solvents, there will be no cross sensitivities. Isopropyl alcohol cannot be detected any longer. Solvents such as isopropyl alcohol lead to interfering signals with undoped systems.

If an alcohol was used as a dopant instead of acetone, clustering and declustering were observed during the drift. The spectra are not stable and analysis is thus very difficult. These analyses were carried out with isopropyl alcohol and ethyl alcohol.

The dopants are advantageously used at constant temperature, e.g., ±0.5° C. The analysis gas flow is to be controlled. The control temperature should be, as a rule, above the highest temperature occurring in the IMS. It is achieved as a result that the rate of permeation of the dopant can be maintained at a constant value with a dopant temperature generated by heating only.

The carrier gas and the drift gas are advantageously identical. The dopant is distributed in the entire inner gas circulation and clusters in the reaction space with the target analyte or target analytes.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which the preferred embodiment of the invention are illustrated.

BRIEF DESCRIPTION OF THE DRAWING

In the drawing:

The only FIGURE is a schematic view of an IMS of the present invention.

DESCRIPTION OF THE PREFERRED EMBODIMENTS

Referring to the drawing in particular, the FIGURE is a schematic view of the spectrometer. The spectrometer comprises an analyzer cell 1 with a sample inlet area 2, with a reaction area 3, with an ionization source 4 in the reaction area, with a closing grid 5, with a drift area 6, with an ionic current detector 7 for detecting ions flowing through the cell drift area, and with a means for measuring the flow times 8 of ions generated in the reaction area of the cell and released through the closing grid 5 into the drift area 6 through the drift area of the cell.

The operating method comprises the following steps: Feeding of an air-drift gas flow into the drift area of the cell; mixing of dopant mixture with the drift gas flow in order to generate a doped drift gas flow; introduction of a gas sample to be analyzed into the analyzer cell inlet area; feeding of a sample gas flow, e.g., as a component flow of the drift gas flow prepared into the inlet area of the cell in order to transport the sample to be analyzed into the reaction area of the cell; measurement of an ionic current at the ionic current detector at a point in time that corresponds to the passage time of the ions generated by the sample to be analyzed in the reaction area of the cell through the drift area of the cell. The dopant used in this method ensures that the ions generated by the carrier gas flow in the reaction area of the cell have passage times through the drift area of the cell that differ from the passage times of the ions generated by the sample to be analyzed through the drift area of the cell.

An IMS operates according to the basic principle of ionizing the analyte substances, of separating them by means of an electrical field imposed from the outside, and of detecting them at the end of the field. The essential components of an IMS are the sample gas inlet system, the ion sources, the reaction space with a closing grid, the drift space and the (ion) collector.

The sample gas inlet system can be characterized by a separating membrane, optionally heated, which separates the environment from the reaction space; a capillary, optionally heated; and a sample loop, optionally heated, which is scavenged over a certain time and whose contents are then fed into the reaction space. A pinhole, which can be induced to vibrate, can assume the task of pumping the sample gas into the reaction space. However, it is also possible to use a gas chromatograph as an inlet system (GC IMS).

A radioactive source, usually 63Ni, 241Am or 3H, a corona discharge source, a laser ionization source or a UV lamp may be an ion source.

A high-voltage supply unit 9 for generating the electrical field from the reaction space 3 to the end of the drift space 6; a grid controller; an internal or external source 10 of pure drift gas, which is pumped against the ionic current from a drift gas inlet 11 to a drift gas outlet 12; a volume flow sensor 13; a temperature sensor 14 and a pressure measuring sensor 15; a rapid narrow-band electrometer 16 for measuring the signals in the pA range; as well as a digital computing unit 17 additionally belong to the IMS. The drift gas source 10 contains a drift gas preparation and doping unit.

Water molecules are at first ionized in undoped systems in the reaction space, in which the ion source is also present, which will subsequently lead to an accumulation of water clusters. Reclustering, during which water clusters are replaced by dopant clusters, takes place in doped systems due to the dopant.

The gas to be analyzed is sent into the reaction space and forms product ions there, which are driven after a grid opening pulse to a flat plate, the Faraday cup, by means of a strong electric field of typically 100 V/cm to 200 V/cm. The ion/ion clusters are separated in the drift space after the closing grid according to their different charges, weights and sizes. The sensor signal is represented as a time curve of an ionic current, i.e., as a spectrum of substance-specific ionic current peaks.

While a specific embodiment of the invention has been shown and described in detail to illustrate the application of the principles of the invention, it will be understood that the invention may be embodied otherwise without departing from such principles.

What is claimed is:

1. A method, comprising:
   determining an analyte substance or an analyte substance mixture as a component of a gas in the presence of a dopant mixture with an ion mobility spectrometer, said analyte substance or the analyte substance mixture being ammonia and/or N-methyl-2-pyrrolidone, said dopant mixture comprising at least one phosphate ester and at least one ketone.

2. A method in accordance with claim 1, wherein said at least one phosphate ester is used at an analysis gas concentration of 5 to 50 $pg/m^3$.

3. A method in accordance with claim 1, wherein said at least one phosphate ester is a tri-(C1 to C12 carbon) phosphate ester.

4. A method in accordance with claim 1, wherein said at least one ketone is used at an analyte substance concentration of 100 to 1,000 $pg/m^3$.

5. A method in accordance with claim 1, wherein said at least one ketone is acetone.

6. A method in accordance with claim 1, wherein said at least one phosphate ester is used at an analysis gas concentration of 10 to 20 $pg/m^3$.

7. A method in accordance with claim 1, wherein said at least one ketone is used at an analyte substance concentration of 200 to 400 $pg/m^3$.

8. An ion mobility spectrometer, comprising:
   a dopant mixture comprising at least one phosphate ester and at least one ketone;
   a drift gas;
   an analyzer cell having a reaction area with a sample feed inlet and a drift area, said drift gas flowing through said drift area of said analyzer cell;
   a closing grid located within said analyzer cell, said analyzer cell and said closing grid defining said reaction area and said drift area; and
   a drift gas source feed located at a position outside of said analyzer cell, said dopant mixture mixing with said drift gas to form a dopant circulation gas, said reaction area, said drift area and said drift gas source feed defining a circulation flow path of said dopant circulation gas.

9. An ion mobility spectrometer in accordance with claim 8, wherein said phosphate ester is present at a concentration of 5 to 50 $pg/m^3$ in said drift area.

10. An ion mobility spectrometer in accordance with claim 8, wherein said phosphate ester is a tri-(C1 to C12 carbon atom) phosphate ester.

11. An ion mobility spectrometer in accordance with claim 8, wherein said ketone is present at a concentration of 100 to 1,000 $pg/m^3$ in said drift area.

12. An ion mobility spectrometer in accordance with claim 8, wherein said ketone is acetone.

13. An ion mobility spectrometer in accordance with claim 8, wherein said dopant circulation gas in said analyzer cell is moved in a direction from said drift area to said reaction area.

14. An ion mobility spectrometer in accordance with claim 6, wherein said phosphate ester is present at a concentration of 10 to 20 $pg/m^3$ in said drift area.

15. An ion mobility spectrometer in accordance with claim 6, wherein said phosphate ester is a triethyl phosphate.

16. An ion mobility spectrometer in accordance with claim 6, wherein said ketone is present at a concentration of 200 to 400 $pg/m^3$ in said drift area.

17. A method comprising:
   providing an ion mobility spectrometer comprising an analyzer cell unit having a sample inlet area, a closing grid, said closing grid defining a reaction area of said analyzer unit and a drift area of said analyzer unit;
   providing a dopant mixture comprising at least one phosphate ester and at least one ketone;
   providing a sample gas;
   delivering drift gas into said drift area of said ion mobility spectrometer to form a drift gas flow in said drift area of said ion mobility spectrometer;
   mixing said dopant mixture with said drift gas flow to form a doped drift gas flow;
   delivering said sample gas into said reaction area of said analyzer cell unit of said ion mobility spectrometer such that said sample gas mixes with said doped drift gas flow to form a sample doped drift gas;
   determining an analyte substance or an analyte substance mixture of said sample doped drift gas with said ion mobility spectrometer, said analyte substance or said analyte substance mixture being one or more of ammonia and N-methyl-2-pyrrolidone.

18. A method in accordance with claim 17, wherein said at least one phosphate ester is used at an analysis gas concentration of 5 to 50 $pg/m^3$.

19. A method in accordance with claim 17, wherein said at least one phosphate ester is a tri-(C1 to C12 carbon) phosphate ester.

20. A method in accordance with claim 17, wherein said at least one ketone is used at an analyte substance concentration of 100 to 1,000 $pg/m^3$.

* * * * *